(12) United States Patent
Lu (10) Patent No.: US 11,926,872 B2
(45) Date of Patent: Mar. 12, 2024

(54) METHOD FOR ISOTHERMAL AMPLIFICATION OF NUCLEIC ACID USING PRIMERS TO GENERATE A TANDEM REPEAT SEQUENCE OF A TARGET GENE

(71) Applicant: Xinhua Lu, Shanghai (CN)

(72) Inventor: Xinhua Lu, Shanghai (CN)

( * ) Notice: Subject to any disclaimer, the term of this patent is extended or adjusted under 35 U.S.C. 154(b) by 558 days.

(21) Appl. No.: 16/977,477

(22) PCT Filed: Jun. 18, 2019

(86) PCT No.: PCT/CN2019/091694
§ 371 (c)(1),
(2) Date: Sep. 2, 2020

(87) PCT Pub. No.: WO2020/034746
PCT Pub. Date: Feb. 20, 2020

(65) Prior Publication Data
US 2021/0054456 A1    Feb. 25, 2021

(30) Foreign Application Priority Data
Aug. 14, 2018  (CN) .......................... 201810920360.1

(51) Int. Cl.
*C12Q 1/6876*    (2018.01)
(52) U.S. Cl.
CPC .................. *C12Q 1/6876* (2013.01)
(58) Field of Classification Search
None
See application file for complete search history.

(56) References Cited

U.S. PATENT DOCUMENTS

2004/0115674 A1* 6/2004 Knott .................. C12Q 1/6848
435/6.12

FOREIGN PATENT DOCUMENTS

| CN | 102618627 A | 8/2012 |
|---|---|---|
| CN | 103255227 A | 8/2013 |
| CN | 106148324 A | 11/2016 |
| CN | 107904284 A | 4/2018 |
| CN | 108034700 A | 5/2018 |
| CN | 108359716 A | 8/2018 |
| CN | 108998509 A | 12/2018 |

OTHER PUBLICATIONS

Faltin (Clinical Chemistry 2013 59:11 pp. 1567-1582).*
Olaf Piepenburg et al., DNA Detection Using Recombination Proteins, PLoS Biology, Jul. 2006, pp. 1115-1121, vol. 4, Issue 7.
Chenhao Li et al., INC-Seq: accurate single molecule reads using nanopore sequencing, Giga Science, 2016, 5:34.

* cited by examiner

*Primary Examiner* — Amanda Haney
(74) *Attorney, Agent, or Firm* — Bayramoglu Law Offices LLC (57) ABSTRACT

A primer for isothermal amplification of nucleic acid and its application are described. The primer includes a forward primer and a reverse primer used for amplifying a target gene. The forward primer is a sequence with an exogenous self-paired hairpin structure at the 5' end, or a sequence with a hairpin structure matched with any source sequence in the target gene close to the forward primer end at the 5' end. Nucleic acid amplification technology using the primer of the invention can produce repeated tandem structure of the target gene, and the repetition times can be controlled precisely. The technology can also be applied to the third generation sequencing technology. The amplification steps are not only simple and fast, but also improve sequencing accuracy.

7 Claims, 3 Drawing Sheets

Specification includes a Sequence Listing.

— METHOD FOR ISOTHERMAL AMPLIFICATION OF NUCLEIC ACID USING PRIMERS TO GENERATE A TANDEM REPEAT SEQUENCE OF A TARGET GENE

CROSS REFERENCE TO THE RELATED APPLICATIONS

This application is the national phase entry of International Application No. PCT/CN2019/091694, filed on Jun. 18, 2019, which is based upon and claims priority to Chinese Patent Application No. 201810920360.1, filed on Aug. 14, 2018, the entire contents of which are incorporated herein by reference.

TECHNICAL FIELD

The present invention relates to the technical field of molecular biology, and in particular, to a primer for isothermal amplification of nucleic acid and its application.

BACKGROUND

Nucleic acid amplification technology is widely used in the field of nucleic acid detection, including nucleic acid sequencing. Common nucleic acid amplification techniques include polymerase chain reaction (PCR), isothermal amplification such as recombinase polymerase amplification (RPA) and helicase-dependent amplification (HDA). These techniques can rapidly amplify the number of nucleic acids, but they cannot change the length of nucleic acid, and cannot produce long-chain nucleic acid with head-to-tail tandem structure. Other nucleic acid amplification techniques, such as rolling circle amplification (RCA), loop-mediated isothermal amplification (LAMP), etc., can produce long-chain nucleic acids, but the reaction cannot be controlled, and the number of repeated fragments in the tandem structure cannot be precisely regulated.

Although traditional nucleic acid detection only needs to amplify the number of nucleic acids, it is very useful to generate repeated tandem structures in certain circumstances. For example, in the third generation of nucleic acid sequencing, due to the single-molecule sequencing technology, the sequencing has limited accuracy. At present, both Oxford nanopore technologies (ONT) and PacBio company's sequencing instruments can sequence nucleic acids with an accuracy rate of around 90%, which is not sufficient for certain applications.

Among them, PacBio (Pacific Biology) company adopts the circular consensus sequencing (CCS) mode, that is, the single nucleic acid molecule is repeatedly sequenced to reach a final accuracy rate of more than 99.99%. After ONT sequenced the same DNA double strand separately, it produced two copies. After software calibration, the accuracy rate can be significantly improved to about 96%. Some laboratories use special amplification methods, for example, INC-Seq: accurate single molecular reads using nanopore sequencing (DOI 10.1186/s3742-016-0140-7), to produce more repeats in tandem structure and obtain higher accuracy. However, these methods are difficult to make ubiquitous throughout labs because there are too many steps and the process requires a lot of time and expense. Therefore, the existing amplification techniques cannot produce long-chain nucleic acids with tandem structure, or the length of nucleic acids produced cannot be controlled precisely.

In the third generation sequencing technology, the sequencing accuracy can be improved by repeatedly sequencing the same sequence, but it needs to consume the output flux of the instrument itself. If it is sequenced twice, the final output data will be reduced by about half, and if it is sequenced 10 times, the output data will be reduced by about 90%. Usually, sequencing twice is the most cost-effective mode. It has been suggested that after sequencing repeatedly six times, there is an obvious marginal diminishing effect on improving accuracy. Therefore, it is practical and significant to reasonably control the number of repeats in the amplified fragment, and simplify and accelerate the amplification steps.

SUMMARY

In view of the above defects in the prior art, the purpose of the present invention is to provide a primer for isothermal amplification of nucleic acid and its application.

The purpose of the present invention can be realized by the following technical scheme.

A primer for isothermal amplification of nucleic acid includes a forward primer and a reverse primer used for amplifying a target gene. The forward primer is a sequence with an exogenous self-paired hairpin structure at the 5' end, or a sequence with a hairpin structure matched with any source sequence in the target gene close to the forward primer end at the 5' end.

Preferably, the reverse primer sequence is the same as a downstream primer sequence required for completing the target gene amplification, or the reverse primer sequence is formed by the same sequence of the downstream primer sequence required for completing the target gene amplification and a sequence with an exogenous self-paired hairpin structure at the 5' end of the downstream primer.

Preferably, it can be applied to a method for isothermal amplification of nucleic acid, which can produce amplification product of a tandem repeat sequence of the target gene.

Preferably, the application method includes, but is not limited to, a RPA amplification method, a HDA amplification method and a PCR amplification method.

Preferably, the amplification product is applied to the library preparation of the sequencing instrument.

A method for isothermal amplification of nucleic acid using any of the above primers to generate tandem repeat sequences, including the following steps, S1, forming a DNA target fragment by nucleic acid amplification by an upstream primer and a downstream primer, wherein the target fragment is composed of a sense strand and an antisense strand;

S2, adding forward primer and reverse primer to carry out double primer amplification; wherein, the forward primer is a sequence with an exogenous self-paired hairpin structure at the 5' end, or a sequence with a hairpin structure matched with any source sequence in the target gene close to the forward primer end at the 5' end;

S3, adding the reverse primer again to perform a single primer amplification to form required amplification product with a sense strand and an antisense strand in series on a same strand.

Preferably, when the reverse primer in S2 has the same sequence as the downstream primer sequence, the S2 forms an amplification product where a sequence can be introduced to form a hairpin loop structure at one end, and the S3 forms diploid amplification product with the sense strand and the antisense strand in series on the same strand;

when the reverse primer in S2 is a sequence with an exogenous self-paired hairpin structure at the 5' end, the S2 forms diploid amplification product with the sense strand and the antisense strand in series on the same strand, and the S3 forms tetraploid amplification product with the sense strand and the antisense strand in series on the same strand.

Preferably, when the reverse primer in S2 is a sequence with an exogenous self-paired hairpin structure at the 5' end, the single primer amplification step in S3 is repeated N times. Besides the tetraploid amplification product with the sense strand and the antisense strand in series on the same strand, the S3 will form a variety of polyploid amplification products having repeated series of the sense strand and the antisense strand on the same strand. Each kind of polyploid increases exponentially, and the number ratio of each kind of polyploid will increase with the increase of repetition times, N≥1. For example, when S3 is repeated, the tetraploid amplification product is mainly produced along with certain auxiliary amplification product such as 8-ploid and 16-ploid amplification products; when S3 continues to be repeated, the proportion of 8-ploid and 16-ploid amplification products will be greatly increased, and at the same time, 32-ploid and 64-ploid amplification products will be produced, by analogy, the proportion of the amplification products is limited by amplification efficiency, and it is not limited here.

Preferably, the method for isothermal amplification of nucleic acid by the primer to generate tandem repeat sequences further includes the following steps, S4, regarding the amplification product with repeated series obtained by S3 as a new whole, introducing a new differential sequence at both ends as a new primer, and then performing S2 double primer amplification and S3 single primer amplification steps successively to obtain amplification product with repeated tandem structure more than twice. A method of introducing the differential sequence in S4 includes but is not limited to connecting a Y-type adapter through ligation reaction, and the differential sequence is the new primer in S4 amplification.

The remarkable advantages of the present invention are as follows.

1. The nucleic acid amplification technology using the primer of the present invention can produce repeated tandem structure of the target gene, and the repetition times can be controlled precisely, such as 2 times, 4 times, 8 times and so on.

2. This technology can also be applied to the third generation sequencing technology. The amplification steps are not only simple and fast, but also can improve the accuracy of sequencing. For example, the sequencing instruments of ONT company uses a modified primer for amplification, and amplification product can be directly combined with the sequencing primer through chemical methods, which saves steps of ligation reaction, and reduces time consumption from 60 minutes to 5 minutes, significantly improving efficiency.

The present invention is further described in combination with drawings of the embodiments, so as to make the technical scheme of the present invention easier to understand and master.

DETAILED DESCRIPTION OF THE EMBODIMENTS

The present invention discloses a primer for isothermal amplification of nucleic acid and its application. The primer includes a forward primer and a reverse primer used for amplifying a target gene. The forward primer is a sequence with an exogenous self-paired hairpin structure at the 5' end, or a sequence with a hairpin structure matched with any source sequence in the target gene close to the forward primer end at the 5' end. The reverse primer sequence is the same as a downstream primer sequence required for completing the target gene amplification, or the reverse primer sequence is formed by the same sequence of the downstream primer sequence required for completing the target gene amplification and a sequence with an exogenous self-paired hairpin structure at the 5' end of the downstream primer. The primer for isothermal amplification of nucleic acid can be used in a RPA amplification method, a HDA amplification method and a PCR amplification method to produce the amplification product of tandem repeat sequence of the target gene.

In order to better understand the present invention, firstly, the characteristics of RPA technology are introduced. In the traditional PCR method, the double strand of template DNA is opened by increasing the temperature to 95° C. in each cycle. When the temperature drops to 60° C., the primer is combined with the matching part of the template DNA (deoxyribonucleic acid). In the reaction process of RPA, there is no need for heating to open the double strand. At room temperature, such as 37° C., recombinant enzyme will bind the primer to scan in the template DNA double strand. After finding the complementary matching sequence, a replacement reaction occurs and the primer is combined. At the same time, the DNA polymerase with an ability of strand displacement begins to synthesize new DNA.

Figure 1:
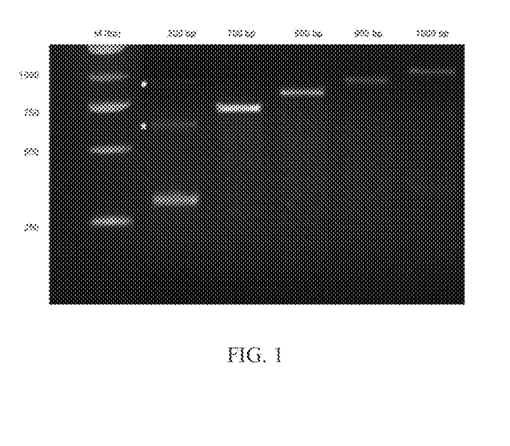
FIG. 1 is an electrophoretic gel map of amplification product in RPA technology mentioned in the present invention.

In the first publication of RPA technology (PLoS Biol. 2006 July; 4(7):e204. DNA detection using recombination proteins), in the supplementary chart of the literature, reproduced here as FIG. 1, the abscissa is the expected length of the target band, M is the reference DNA, and the ordinate is the length of the reference DNA band. On the electrophoretic gel map of the amplification product, the author used "*" to mark some DNA bands that have a length different from an expected length, which are twice and three times of the expected length. The author speculated that these products were generated due to non-specific amplification caused by the formation of self-paired hairpin structure. These products, which are twice and three times the length of the target nucleic acid, are to be avoided in traditional RPA amplification, and they are also weak and unstable. However, they reveal the potential of the RPA amplification. Based on this technical solution, a new primer is designed, and amplification product with increased nucleic acid length is achieved through the RPA technology. Of course, it can also be achieved through HDA technology, or through amplification reaction where the primer continuously binds to the target fragment under the participation of other DNA polymerases with strand displacement capabilities.

1. Firstly, Amplifying the Target DNA Fragment to Form Products of a Sense Strand and an Antisense Strand Tandem Structure.

Figure 2:
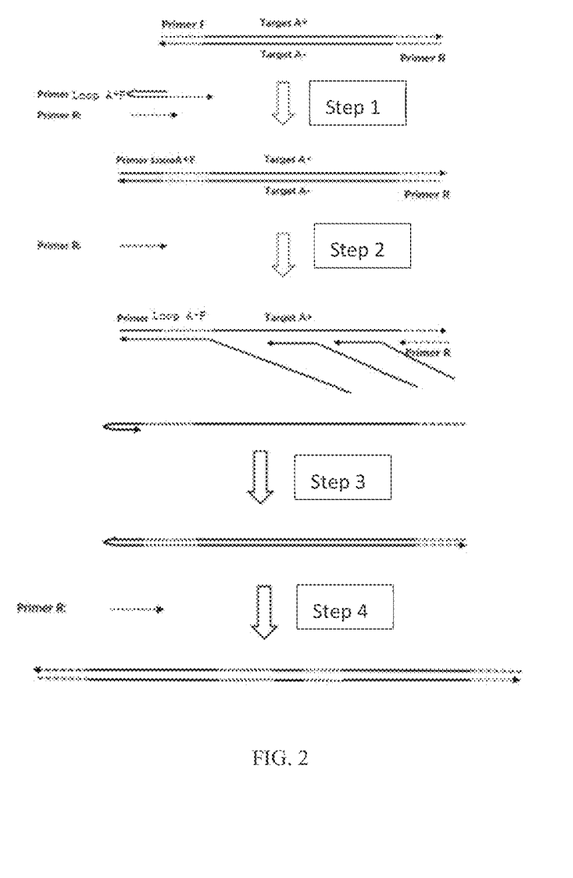
FIG. 2 is a schematic diagram showing steps of nucleic acid amplification using a primer of the present invention, wherein a forward primer is a primer with a hairpin structure.

Referring to FIG. 2, the DNA target fragment (Target A+ is a sense strand, Target A− is an antisense strand) is amplified by a forward primer (Primer F) and a reverse primer (Primer R).

Step 1, the reverse primer and a new forward primer (Primer Loop A+F) are added to the RPA reaction. The 3' end sequence of the new forward primer is consistent with that of primer F, and the 5' end sequence may form a hairpin shaped loop. The amplification product of step 1 introduces a sequence, which can form a hairpin loop at one end.

Step 2, only the reverse primer is added to the RPA reaction to perform a single primer amplification. Target A+ is used as a template in the amplification reaction to produce Target A− continuously.

Step 3, the newly generated Target A− can form a hairpin loop at the 3' end, which can be further synthesized using itself as a template. The product is a self-paired, semi-closed, DNA single strand.

Step 4, the reverse primer continues to participate in the RPA reaction. The 5' end of the new amplification product is a Target A− sequence and the 3' end is a double strand of the Target A+ sequence, which is about twice the length of the target fragment.

By designing the primer, which can form the hairpin structure on one side of the target fragment, and using the primer on the other side to perform the single primer RPA amplification, the amplification product of the sense strand in series with the antisense strand is stably generated.

In order to form the hairpin structure, the primer can carry a reverse complementary sequence at the 5' end, or a sequence at the 5' end which can be inversely complementary to a certain part of an internal sequence of an amplicon close to the 5' end.

2. Amplifying the Target DNA Fragment to Form Products of the Sense Strand and the Antisense Strand Multiple Repeated Tandem Structure.

As shown in FIG. 2, according to the above method, the target fragment can be amplified into the amplification product of the sense strand and the antisense strand in series, and the amplification product can be regarded as a new target fragment. By introducing new similar sequences on both sides. For example, by adding a new adapter sequence through ligation reaction, the amplification product of an original target fragment with the sense strand and the antisense strand repeated twice can be amplified. In the same way, repeat this step to amplify $2^n$-repeated amplification product, where n is an arbitrary integer. In practice, n is limited by amplification efficiency.

3. Quickly Amplifying the Target DNA Fragment to Form Products of the Sense Strand and the Antisense Strand Tandem Structure.

In order to quickly obtain the amplification products of the sense strand in series with the antisense strand, forward and reverse amplification primers with hairpin structure can also be used.

Figure 3:
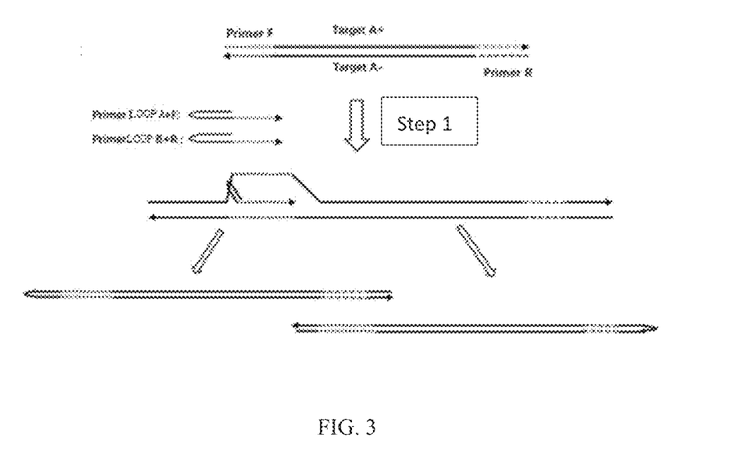
FIG. 3 is a schematic diagram showing the steps of nucleic acid amplification using a primer of the present invention, wherein a forward primer and a reverse primer are primers with a hairpin structure.

As shown in FIG. 3, the 5' end of the primer is a closed loop structure, and it is self-paired, so that once the complementary structure of the 3' end of the complementary strand is exposed, it has to be self-paired, and then uses itself as a template for amplification, forming a sense strand in series with antisense strand, semi-closed, DNA single strand. At the same time, after a new strand generated by extension of a new primer is displaced and dissociated, it will be self-paired at the 3' end and amplified with itself as a template to form a sense chain in series with antisense chain, semi-closed, DNA single strand.

Therefore, the product after amplification is directly the sense strand in series with antisense strand, semi-closed, DNA single strand (diploid, a new DNA fragment formed by connecting the sense strand and the antisense strand of the target DNA fragment in tandem one time). Since diploid product can be amplified, there will be longer amplification product, such as tetraploid (a new DNA fragment formed by connecting the sense strand and the antisense strand of the target DNA fragment in tandem two times), hexaploid (a new DNA fragment formed by connecting the sense strand and the antisense strand of the target DNA fragment in tandem three times), and octoploid (a new DNA fragment formed by connecting the sense strand and the antisense strand of the target DNA fragment in tandem four times). They are all integral multiples of 2, but limited by the amplification efficiency, diploids account for the majority. If the amplification primer is added in batches and many times, the amount of polyploids may be significantly increased.

4. Amplifying the Target DNA Fragment to Form Products of the Sense Strand and the Antisense Strand Twice Repeated Tandem Structure.

Figure 4:
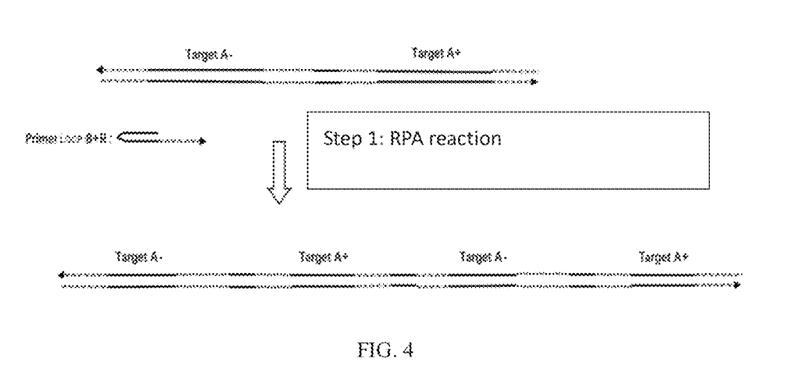
FIG. 4 is a schematic diagram showing steps of amplifying polyploid-based amplification product that is repeated twice in series.

As shown in FIG. 4, the starting fragment is the amplification product of FIG. 2, mainly the diploid of the sense strand in series with the antisense strand. If the reverse primer with hairpin structure is continued to be added after the reaction is finished, and the single primer amplification is carried out, the tetraploid-based amplification product can continue to be obtained. Alternatively, in the steps shown in FIG. 2, the reverse primer with hairpin structure can be directly used. After amplification is finished, the products are mainly tetraploid. Similarly, the amplification product in FIG. 3 can be subjected to a single primer amplification by using the forward or reverse primer with hairpin structure again, and the tetraploid amplification product repeated twice can be obtained.

5. Obtaining Amplification Products with Tandem Structure by HDA.

This technical scheme can also be realized by HDA. Firstly, technical characteristics of HDA are introduced. The amplification process of HDA can be divided into six stages: (i) DNA double strand unwinding by helicase, (ii) binding and maintaining single strand by single-stranded binding protein, (iii) primer binding, (iv) polymerase binding, (v) catalytic target sequence synthesis, and (vi) new strand unwinding by helicase for recycling. At the beginning of the reaction, helicase binds to double-stranded DNA with the aid of a helper protein, and begins to break the double-stranded DNA into single-strand DNA with the participation of ATP. The single-stranded DNA is immediately bound by the single-stranded binding protein in the system, stabilizing the newly unwound DNA single-strand and preventing the re-formation of double strands. After the single-stranded template is formed, the primer binds to the target sequence. At the same time, polymerase binds and catalyzes the synthesis of the target sequence. Newly synthesized sequence enters a new round of unwinding and amplification cycling. After continuous circulation, the target sequence is amplified exponentially, and the product is the same as the product of conventional PCR, which is double-stranded target DNA.

At the same temperature, the HDA reaction can complete the DNA strand displacement and synthesis, and at the same time, complete the binding of the new primer to the template to initiate a new synthesis reaction. Therefore, the same primer and steps as RPA can be used to obtain amplification fragment with the sense strand in series with antisense strand repeated one or more times.

However, the helicase in the system can also unwind the double-stranded DNA without primer in the HDA reaction, so dynamic separation and binding of the double-stranded DNA will occur. When there is a self-complementary palindrome sequence at the 3' end, in the process of double-strand separation to re-pairing, there is a certain probability to form a complete match between the sense strand and the antisense strand, and there is also a certain probability that the palindrome sequence of each strand can form a stem-loop structure, and the stem-loop structure at the 3' end can trigger a new amplification, using itself as a template to double the length.

If there is a sequence on both sides of the target DNA fragment that can form the stem-loop structure, similar to the amplification product in FIG. 3, then the target fragment can be lengthened spontaneously without primer, and the amplification fragment of the sense strand in series with antisense strand repeated many times is obtained. The number of repeats is related to the reaction time.

Therefore, when using HDA technology for amplification, if the single primer used in single primer amplification has no stem-loop structure, the reaction can control the fragment length like RPA reaction. If the amplification primer adopts a stem-loop structure, the reaction can still increase the fragment length when the primer is exhausted, and more repeats will occur with the extension of amplification time.

Embodiment 1

This embodiment will illustrate that long DNA fragments with sense strands in series with antisense strands of a target gene can be amplified by two-step RPA reaction with hairpin structure primer.

Forward primer: 5'-CCACTTCAGCACGAGATGCGG-TGGC-3' (as shown in SEQ ID NO. 1), and reverse primer: 5'-GCGATGCTGATACCGCACTTCCCGC-3' (as shown in SEQ ID NO. 2), a 276 bp amplicon amplified by PCR from Lambda standard DNA is used as a target segment, and the sequence of the amplicon is as follows (as shown in SEQ ID NO. 3):

CCACTTCAGCACGAGATGCGGTGGCCTCAAAAGAGGCAGCAAAATCA

TCAGAAACGAACGCATCATCAAGTGCCGGTCGTGCAGCTTCCTCGGCAAC

GGCGGCAGAAAATTCTGCCAGGGCGGCAAAAACGTCCGAGACGAATGCC

AGGTCATCTGAAACAGCAGCGGAACGGAGCGCCTCTGCCGCGGCAGACG

CAAAAACAGCGGCGGCGGGGAGTGCGTCAACGGCATCCACGAAGGCGAC

AGAGGCTGCGGGAAGTGCGGTATCAGCATCGC

A new forward primer (as shown in SEQ ID NO. 4):

5'-CGTAGCTGATGGCACATATGTGCCATCAGCTACGCCACTTCAGCACG
AGATGCGGTGGC-3' and the reverse primer are used to perform RPA reaction on the target fragment. RPA reagent is purchased from TwistDX company in UK, and its name is TwistAmp Basic reagent.

The first step reaction system is 50 ul, containing TwistAmp Basic powder, 2.4 ul forward amplification primer (10 uM), 2.4 ul reverse amplification primer (10 uM), 29.5 ul reaction buffer, 1 ul (about 1 nM) target fragment, 2.5 ul (280 mM) magnesium acetate, and 12.2 ul water. Reaction conditions: 37° C., 40 minutes.

The second step reaction system is 50 ul, containing TwistAmp Basic powder, 4.8 ul (10 uM) reverse amplification primer, 29.5 ul reaction buffer, 1 ul 100 times dilution of the amplification product from the first step, 2.5 ul (280 mM) magnesium acetate and 12.2 ul water. Reaction conditions: 37° C., 40 minutes.

The final amplification product is detected by electrophoresis, and there are bright bands at about 300 bp and 600 bp.

Figure 5:
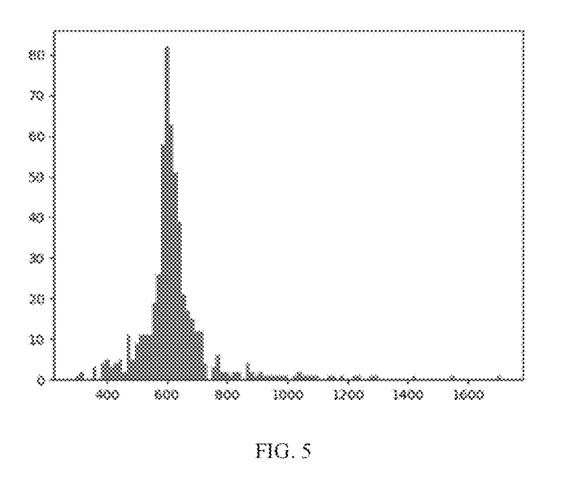
FIG. 5 is a diagram of sequencing read length in embodiment 1 of the present invention.

The amplification product is sequenced in the third generation (ONT instrument) and detected by ligation method, and the length is concentrated at 600 bp. As shown in FIG. 5, the abscissa represents sequencing length, and the ordinate represents sequencing quantity. Due to the high error rate, especially missing errors, of the third generation sequencing, the length cannot be measured accurately, so it is a graph similar to normal distribution.

Conclusion: 1. The amplification product is long DNA fragments with sense strands in series with antisense strands. 2. The band at about 300 bp on the electrophoresis gel corresponds to sense strands in series with antisense strands, self-paired, semi-closed, DNA single strands. The band at about 600 bp on the electrophoresis gel correspond to flattened DNA double strands with sense strands in series with antisense strands.

Embodiment 2

This embodiment will illustrate that long DNA fragments with sense strands in series with antisense strands of a target gene can be amplified by one-step RPA reaction with hairpin structure primer.

Forward primer: 5'-CCACTTCAGCACGAGATGCGGT-GGC-3' (as shown in SEQ ID NO. 1), and reverse primer: 5'-GCGATGCTGATACCGCACTTCCCGC-3' (as shown in SEQ ID NO. 2), a 276 bp amplicon amplified by PCR from Lambda standard DNA is used as a target segment, and the sequence of the amplicon is as follows (as shown in SEQ ID NO. 3):

CCACTTCAGCACGAGATGCGGTGGCCTCAAAAGAGGCAGCAAAATCA

TCAGAAACGAACGCATCATCAAGTGCCGGTCGTGCAGCTTCCTCGGCAAC

GGCGGCAGAAAATTCTGCCAGGGCGGCAAAAACGTCCGAGACGAATGCC

AGGTCATCTGAAACAGCAGCGGAACGGAGCGCCTCTGCCGCGGCAGACG

CAAAAACAGCGGCGGCGGGGAGTGCGTCAACGGCATCCACGAAGGCGAC

AGAGGCTGCGGGAAGTGCGGTATCAGCATCGC

A new forward primer (as shown in SEQ ID NO. 4):

5'-CGTAGCTGATGGCACATATGTGCCATCAGCTACGCCACTTCCAGCAC

GAGATGCGGTGGC-3' and a new reverse primer (as shown in SEQ ID NO. 5):

5'-GGCTGCAAGCCCGATAATTATCGGGCTTGCAGCGCGATGCTGATACC

GCACTTCCCGC-3' are used to perform RPA reaction on the target fragment. RPA reagent is purchased from TwistDX company in UK, and its name is TwistAmp Basic reagent.

The reaction system is 50 ul, containing TwistAmp Basic powder, 2.4 ul (10 uM) forward amplification primer, 2.4 ul (10 uM) reverse amplification primer, 29.5 ul reaction buffer, 1 ul (about 1 nM) target fragment, 2.5 ul (280 mM) magnesium acetate, and 12.2 ul water. Reaction conditions: 37° C., 40 minutes.

The final amplification product is detected by electrophoresis, and there are bright bands at about 300 bp and 600 bp.

Figure 6:
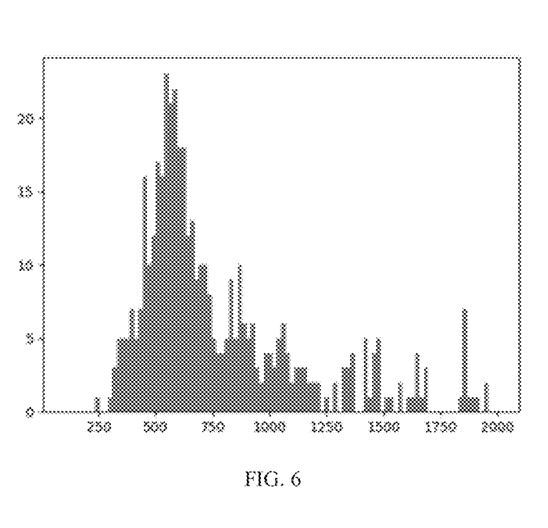
FIG. 6 is a diagram of sequencing read length in embodiment 2 of the present invention.

The amplification product is sequenced in the third generation (ONT instrument) and detected by ligation method, and a peak of the length appears at 600 bp. As shown in FIG. 6, the abscissa represents sequencing length, and the ordinate represents sequencing quantity. Due to the high error rate, especially missing errors, of the third generation sequencing, the length cannot be measured accurately, so it is a graph similar to normal distribution at 600 bp, and the longer part of the sequence also has a small amount of distribution.

Conclusion: 1. The amplification product is mainly long DNA fragments with sense strands in series with antisense strands (diploid), and there is also a small number of product that is repeated series (tetraploid, octoploid, etc.). 2. The band at about 300 bp on the electrophoresis gel corresponds to sense strands in series with antisense strands, self-paired, semi-closed, DNA single strands. The band at about 600 bp on the electrophoresis gel corresponds to flattened DNA double strands with sense strands in series with antisense strands. The amplification products of other length are not obviously shown on the gel map because of their small quantity.

Embodiment 3

This embodiment will illustrate that long DNA fragments with sense strands in series with antisense strands repeated many times of a target gene can be amplified by adding the primer many times in the RPA reaction with hairpin structure primer.

Forward primer: 5'-GGAAAGTGTTCGACGGTGAGCTGAG-3' (as shown in SEQ ID NO. 6), and reverse primer: 5'-ATACTGTCATCAGCATTACGTCATC-3' (as shown in SEQ ID NO. 7), a 405 bp amplicon amplified by PCR from Lambda standard DNA is used as a target segment, and the sequence of the amplicon is as follows (as shown in SEQ ID NO. 8):

GGAAAGTGTTCGACGGTGAGCTGAGTTTTGCCCTGAAACTGGCGCGT

GAGATGGGGCGACCCGACTGGCGTGCCATGCTTGCCGGGATGTCATCCAC

GGAGTATGCCGACTGGCACCGCTTTTACAGTACCCATTATTTTCATGATG

TTCTGCTGGATATGCACTTTTCCGGGCTGACGTACACCGTGCTCAGCCTG

TTTTTCAGCGATCCGGATATGCATCCGCTGGATTTCAGTCTGCTGAACCG

GCGCGAGGCTGACGAAGAGCCTGAAGATGATGTGCTGATGCAGAAAGCGG

CAGGGCTTGCCGGAGGTGTCCGCTTTGGCCCGGACGGGAATGAAGTFATC

CCCGCTTCCCCGGATGTGGCGGACATGACGGAGGATGACGTAATGCTGAT

GACAGTAT

A new forward primer (as shown in SEQ ID NO. 9):

5'-TATATATATATATATATATATATATATATAGGGAAGCTTGGAAAGTG

TTCGACGGTGAGCTGAG-3' and a new reverse primer (as shown in SEQ ID NO. 10):

5'-TATATATATATATATATATATATATATATAGGGAAGCTTATACTGTC

ATCAGCATTACGTCATC-3' are used to perform RPA reaction on the target fragment. RPA reagent is purchased from TwistDX company in UK, and its name is TwistAmp Basic reagent.

The reaction system is 50 ul, containing TwistAmp Basic powder, 1 ul (10 uM) forward amplification primer, 1 ul (10 uM) reverse amplification primer, 29.5 ul reaction buffer, 1 ul (about 1 nM) target fragment, 2.5 ul (280 mM) magnesium acetate, and 12.2 ul water. Reaction conditions: 37° C., 150 minutes.

In the reaction process, amplification primer mixture (including forward amplification primer (5 uM) and reverse amplification primer (5 uM)) is added. Specifically, 2 ul of the amplification primer mixture is added at the 20th minute, the 40th minute, the 60th minute, and the 80th minute, respectively.

The electrophoresis gel map of the final amplification product shows clear bands at about 450 bp, 900 bp, 1350 bp and 1800 bp, and diffuse bands from 5000 bp to the sample port.

The amplification product is sequenced in the third generation (ONT instrument) and detected by breaking method, sequencing structure shows that most of them are tandem structures repeated within 6 times, but high-multiple repeat sequences with reading length more than 5000 bp account for about 5%.

Conclusion: The amplification product is long DNA fragments with sense strands in series with antisense strands, the number of repeats in series is widely distributed, and there are high-multiple repeat sequences.

There are still many embodiments of the present invention, and all technical solutions formed by equivalent transformation/conversion are within the protection scope of the present invention.

What is claimed is:

1. A method of performing isothermal amplification on a target gene to form an amplification product with a sense strand and an antisense strand in series for one time on the same strand comprising the following steps:
(S1) preparing a target gene DNA fragment, wherein the target gene DNA fragment is composed of a sense strand and an antisense strand;
(S2) adding a forward primer and a reverse primer to carry out a double primer isothermal amplification, wherein the forward primer is a sequence with an exogenous self-paired hairpin structure at the 5' end, or a sequence with a hairpin structure matched with a source sequence in the target gene adjacent to the forward primer end at the 5' end; and (S3) adding the reverse primer again to perform a single primer isothermal amplification to form a diploid amplification product with the sense strand and the antisense strand in series for one time on the same strand.

2. The method according to claim 1, wherein the isothermal amplification is RPA amplification or HDA amplification.

3. The method according to claim 1, wherein the diploid amplification product is applied to a library preparation of a sequencing instrument.

4. A method of performing isothermal amplification of a target gene to form a tandem repeat amplification product with a sense strand and an antisense strand in series on the same strand for a plurality of times comprising the following steps:
(S10) preparing a target gene DNA fragment, wherein the target gene DNA fragment is composed of a sense strand and an antisense strand;
(S20) adding a forward primer and a reverse primer to carry out a double primer isothermal amplification wherein, each of the primers is a sequence with an exogenous self-paired hairpin structure at the 5' end, or a sequence with a hairpin structure matched with a source sequence in the target gene adjacent to the forward primer end at the 5' end; the (S20) forms a diploid amplification product with the sense strand and the antisense strand in series for one time on the same strand;
(S30) adding the reverse primer again to perform a single primer isothermal amplification to form a tetraploid amplification product with the sense strand and the antisense strand in series for two times on the same strand; and
(S40) adding the reverse primer again to perform a single primer isothermal amplification, wherein (S40) is repeated N times to form a variety of polyploid amplification products with the sense strand and the antisense strand in series for a plurality of times on the same strand, wherein each of the polyploid amplification products increases exponentially, and a number ratio of each of the polyploid amplification products increases with an increase of repetition times, N≥1.

5. The method according to claim 4, further comprising connecting a Y type adapter through ligation reaction to the variety of polyploid amplification products with the sense strand and the antisense strand in series for a plurality of times on the same strand and then repeating the double primer amplification of (S20) and the single primer amplification of (S30) using new primers that hybridize to the Y type adapters at least two times.

6. The method according to claim 4, wherein the isothermal amplification is RPA amplification or HDA amplification.

7. The method according to claim 4, wherein the tandem repeat amplification product is applied to a library preparation of a sequencing instrument.

\* \* \* \* \*

SEQUENCE LISTING

<160> NUMBER OF SEQ ID NOS: 10

<210> SEQ ID NO 1
<211> LENGTH: 25
<212> TYPE: DNA
<213> ORGANISM: Artificial Sequence
<220> FEATURE:
<223> OTHER INFORMATION: Primer F in Example 1 and 2

<400> SEQUENCE: 1
ccacttcagc acgagatgcg gtggc                                        25

<210> SEQ ID NO 2
<211> LENGTH: 25
<212> TYPE: DNA
<213> ORGANISM: Artificial Sequence
<220> FEATURE:
<223> OTHER INFORMATION: Primer R in Example 1 and 2

<400> SEQUENCE: 2
gcgatgctga taccgcactt cccgc                                        25

<210> SEQ ID NO 3
<211> LENGTH: 276
<212> TYPE: DNA
<213> ORGANISM: Artificial Sequence
<220> FEATURE:
<223> OTHER INFORMATION: Amplicon amplified from the lambda DNA standard
      as a target fragment in Example 1 and 2

<400> SEQUENCE: 3
ccacttcagc acgagatgcg gtggcctcaa aagaggcagc aaaatcatca gaaacgaacg    60
catcatcaag tgccggtcgt gcagcttcct cggcaacggc ggcagaaaat tctgccaggg   120
cggcaaaaac gtccgagacg aatgccaggt catctgaaac agcagcggaa cggagcgcct   180
ctgccgcggc agacgcaaaa acagcggcgg cgggagtgc gtcaacggca tccacgaagg    240
cgacagaggc tgcgggaagt gcggtatcag catcgc                            276

<210> SEQ ID NO 4
<211> LENGTH: 59
<212> TYPE: DNA
<213> ORGANISM: Artificial Sequence
<220> FEATURE:
<223> OTHER INFORMATION: Primer LoopA+F in Example 1 and 2

<400> SEQUENCE: 4
cgtagctgat ggcacatatg tgccatcagc tacgccactt cagcacgaga tgcggtggc    59

<210> SEQ ID NO 5
<211> LENGTH: 59
<212> TYPE: DNA
<213> ORGANISM: Artificial Sequence
<220> FEATURE:
<223> OTHER INFORMATION: Primer Loop B+R in Example 2

<400> SEQUENCE: 5
ggctgcaagc ccgataatta tcgggcttgc agccgcgatg ctgataccgc acttcccgc    59

<210> SEQ ID NO 6
<211> LENGTH: 25
<212> TYPE: DNA
<213> ORGANISM: Artificial Sequence
<220> FEATURE:
<223> OTHER INFORMATION: Primer F in Example 3

<400> SEQUENCE: 6
ggaaagtgtt cgacggtgag ctgag                                          25

<210> SEQ ID NO 7
<211> LENGTH: 25
<212> TYPE: DNA
<213> ORGANISM: Artificial Sequence
<220> FEATURE:
<223> OTHER INFORMATION: Primer R in Example 3

<400> SEQUENCE: 7
atactgtcat cagcattacg tcatc                                          25

<210> SEQ ID NO 8
<211> LENGTH: 405
<212> TYPE: DNA
<213> ORGANISM: Artificial Sequence
<220> FEATURE:
<223> OTHER INFORMATION: Amplicon amplified from the Lambda DNA standard
      as a target fragment in Example 3

<400> SEQUENCE: 8
ggaaagtgtt cgacggtgag ctgagttttg ccctgaaact ggcgcgtgag atggggcgac    60
ccgactggcg tgccatgctt gccgggatgt catccacgga gtatgccgac tggcaccgct   120
tttacagtac ccattatttt catgatgttc tgctggatat gcacttttcc gggctgacgt   180
acaccgtgct cagcctgttt ttcagcgatc cggatatgca tccgctggat ttcagtctgc   240
tgaaccggcg cgaggctgac gaagagcctg aagatgatgt gctgatgcag aaagcggcag   300
ggcttgccgg aggtgtccgc tttggcccgg acgggaatga agttatcccc gcttccccgg   360
atgtggcgga catgacggag gatgacgtaa tgctgatgac agtat                   405

<210> SEQ ID NO 9
<211> LENGTH: 64
<212> TYPE: DNA
<213> ORGANISM: Artificial Sequence
<220> FEATURE:
<223> OTHER INFORMATION: Primer LoopA+F in Example 3

<400> SEQUENCE: 9
tatatatata tatatata tatatata gggaagcttg gaaagtgttc gacggtgagc       60
tgag                                                                 64

<210> SEQ ID NO 10
<211> LENGTH: 64
<212> TYPE: DNA
<213> ORGANISM: Artificial Sequence
<220> FEATURE:
<223> OTHER INFORMATION: Primer LoopB+R in Example 3

<400> SEQUENCE: 10
tatatatata tatatata tatatata gggaagctta tactgtcatc agcattacgt       60
catc                                                                 64